(12) United States Patent
Matsuoka et al.

(10) Patent No.: US 8,372,256 B2
(45) Date of Patent: Feb. 12, 2013

(54) GAS SENSOR ELEMENT AND GAS SENSOR EQUIPPED WITH THE SAME

(75) Inventors: Hiroshi Matsuoka, Kariya (JP); Tetsuya Kato, Okazaki (JP); Makoto Nakae, Nagoya (JP); Syuuichi Nakano, Kariya (JP)

(73) Assignees: Nippon Soken, Nishio (JP); Denso Corporation, Kariya (JP)

( * ) Notice: Subject to any disclaimer, the term of this patent is extended or adjusted under 35 U.S.C. 154(b) by 535 days.

(21) Appl. No.: 12/644,675

(22) Filed: Dec. 22, 2009

(65) Prior Publication Data

US 2010/0155240 A1    Jun. 24, 2010

(30) Foreign Application Priority Data

Dec. 22, 2008 (JP) ................................ 2008-325285
Oct. 5, 2009 (JP) ................................ 2009-231197

(51) Int. Cl.
*G01N 27/407* (2006.01)
(52) U.S. Cl. .................... 204/424; 204/410; 73/23.31
(58) Field of Classification Search .................. 204/429, 204/410, 411, 421, 424–428; 205/783.5–785; 73/23.31–23.33
See application file for complete search history.

(56) References Cited

U.S. PATENT DOCUMENTS

| | | |
|---|---|---|
| 5,593,558 A | 1/1997 | Sugino et al. |
| 5,800,689 A | 9/1998 | Hori et al. |
| 7,329,844 B2 | 2/2008 | Kojima et al. |

FOREIGN PATENT DOCUMENTS

| | | |
|---|---|---|
| JP | 07-333191 | 12/1995 |
| JP | 08-240559 | 9/1996 |
| JP | 2001-281210 | 10/2001 |
| JP | 2006-126077 | 5/2006 |
| JP | 2007-121323 | 5/2007 |

OTHER PUBLICATIONS

H. Li and X.C. Zeng, "Wetting and Interfacial Properties of Water Nanodroplets in Contact with Graphene and Monolayer Boron-Nitride Sheets", ACS NANO, vol. 6, No. 3, Mar. 27, 2012, p. 2401-2409.*
A.W. Adamson and A.P. Gast, Table X-2 Selected Contact Angle Data, in Physical Chemistry of Surfaces, Sixth Edition, John Wiley & Sons, Inc., New York: 1997, p. 365-366.*
Japanese Office Action dated Oct. 26, 2010, issued in corresponding Japanese Application No. 2009-231197 with English Translation.

* cited by examiner

*Primary Examiner* — J. Christopher Ball
(74) *Attorney, Agent, or Firm* — Nixon & Vanderhye P.C.

(57) ABSTRACT

A gas sensor element is composed of a sensor section, a heater section, and a porous protective layer. The sensor section is composed of a solid electrolyte layer and a pair of electrodes. The heater section heats the sensor section to activate it. The porous protective layer covers surfaces of the sensor section and the heater section of the gas sensor element in a gas sensor which is exposed to a target detection gas to be detected. The porous protective layer is made of a mixture of hydrophobic heat resisting particles having a contact angle of not less than 75° to a drop of water, and the hydrophilic heat resisting particles having a contact angle not more than 30° to a drop of water. A gas sensor equipped with the above gas sensor element is also disclosed.

10 Claims, 10 Drawing Sheets

GAS SENSOR ELEMENT AND GAS SENSOR EQUIPPED WITH THE SAME

CROSS-REFERENCE TO RELATED APPLICATION

This application is related to and claims priority from Japanese Patent Application Numbers JP 2008-325285, filed on Dec. 22, 2008, and JP 2009-231197, filed on Oct. 5, 2009, the contents of which are hereby incorporated by reference.

BACKGROUND OF THE INVENTION

1. Field of the Invention

The present invention relates to gas sensor elements with improved durability, superior waterproof properties, and improved strength, which is capable of detecting a concentration of a specific gas component contained in a target detection gas, for example, an exhaust gas emitted from an internal combustion engine of a vehicle engine, and also relates to a gas sensor equipped with this gas sensor element.

2. Description of the Related Art

There is a gas sensor placed in an exhaust gas passage equipped with an exhaust gas purifying apparatus through which a target detection gas flows. For example, the target detection gas is an exhaust gas emitted from an internal combustion engine such as a vehicle engine. Such a gas sensor placed in the exhaust gas passage of the internal combustion engine detects a concentration of a specific gas component contained in an exhaust gas in order to control the combustion state of the internal combustion engine or the operation of the exhaust gas purifying apparatus. There are oxygen, nitrogen oxide, ammonia, and hydrogen as the specific gas component to be detected.

There is an oxygen sensor as the above gas sensor, for example. This oxygen sensor is equipped with a multilayered type gas sensor element which has a lamination structure comprised of a solid electrolyte body, a detection electrode layer, a porous diffusion resistance layer, a reference electrode layer, a reference electrode chamber formation layer, and an insulation base body. When the gas sensor is an oxygen gas sensor, the solid electrolyte body has an oxygen ion conductivity. For example, the oxygen gas sensor has a plate-like shape. The detection electrode layer is formed on one surface of the solid electrolyte body, and contacts with a target detection gas. The porous diffusion resistance layer is formed at the detection electrode layer side of the gas sensor. The target detection gas to be detected is passed through the porous diffusion resistance layer in the gas sensor. The reference electrode layer is formed on the other surface of the solid electrolyte body, and contacts with a reference gas. The reference gas chamber formation layer has a reference gas chamber, and is formed at the reference electrode layer side. The reference gas is introduced into the reference gas chamber. The insulation base body has an embedded heater therein. In the multilayered type gas sensor element having a lamination structure, the solid electrolyte body, the detection electrode layer, the porous diffusion resistance layer, the reference electrode layer, the reference electrode chamber formation layer, and the insulation base body are laminated as described above.

In general, the exhaust gas emitted from the internal combustion engine contains oil-containing components and sensor-poisoning materials, where the oil-containing components are P, Ca, Zn, Si, etc, and the poisoning materials are made of additives such as K, Na, and Pb which are added into gasoline as a fuel. Those poisoning materials such as K, Na, and Pb contaminate the detection electrode layer and the porous diffusion resistance layer in the gas sensor element. This contamination often causes deterioration of the response capability and an output error of the gas sensor.

In addition, the exhaust gas generally contains water vapor component. Condensing the water vapor contained in the exhaust gas generates drops of water, and the drops of water are often adhered onto the surface of the multilayered type gas sensor element in the gas sensor.

In general, such a multilayered type gas sensor element having the above a lamination structure is used under a high temperature condition of not less than 700° C. because of being heated by the embedded heater, for example, in order to show an ion conductivity of the solid electrolyte body to a specific ion.

There is thereby a possibility of breaking the multilayered type gas sensor element by the large thermal shock generated when drops of water contained in the target detection gas contact to the surface of the multilayered type gas sensor element.

There are known methods in order to avoid the generation of error detection which is caused by trapping poisoning materials contained in the is exhaust gas as the target detection gas. For example, a conventional method forms a poison trapping layer having a predetermined thickness on the surface of the diffusion resistance layer. This diffusion resistance layer is exposed to the target detection gas (as disclosed in Japanese patent laid open publication No. JP 2006-126077).

Another conventional method forms a porous protective layer having a predetermined thickness on the outer peripheral surface of the gas sensor element in order for a drop of water to diffuse through the inside of the porous protective layer. This structure relaxes a thermal shock and avoids generation of cracks even if the drop of water (or the water drop) contacts to the surface of the gas sensor element (as disclosed in Japanese patent laid open publication No. JP 2007-121323).

However, because a poison trapping layer in the conventional multilayered gas sensor element described above is made of heat resisting particles. The heat resisting particles have a relatively large specific area in order to certainly trap poisoning materials contained in the target detection gas. Because the conventional multilayered gas sensor element easily absorbs the drop of water and thereby causes a lack of dry condition, this structure causes breaking of the gas sensor element when heated at a high temperature in order to activate it.

SUMMARY OF THE INVENTION

It is an object of the present invention to provide a gas sensor element with superior durability having a porous protective layer capable of protecting the gas sensor element from contaminating of poisoning materials and breaking by a drop of water adhered onto the surface of the gas sensor element. It is another object of the invention to provide a gas sensor equipped with the gas sensor element.

To achieve the above purposes, there is provided a gas sensor element, as a first aspect of the invention, capable of detecting a concentration of a is specific gas component contained in a target detection gas. For example, the gas sensor element is incorporated in a gas sensor such as an oxygen sensor, and placed in a gas passage through which the target defection gas flows. The gas sensor element of the first aspect of the invention has a sensor section, a heater section and a porous protective layer. The sensor section has a solid electrolyte layer and a pair of electrodes. The solid electrolyte layer is made of solid electrolyte material having an electrical conductivity to a specific ion. The pair of electrodes is formed on a surface of the solid electrolyte layer. The heater section heats the sensor section in order to activate it. The surface of the sensor section and the surface of the heater section are covered with the porous protective layer, and exposed to the target detection gas. In the gas sensor element, the porous protective layer is made of a mixture composed of at least one kind of hydrophobic heat resisting particles and at least one kind of hydrophilic heat resisting particles. The hydrophobic heat resisting particles and the hydrophilic heat resisting particles have a different contact angle to a drop of water. For example, it is preferable for the hydrophobic heat resisting particles forming the porous protective layer to have a contact angle of not less than 75°. It is further preferable for the hydrophilic heat resisting particles forming the porous protective layer to have a contact angle of not more than 30°.

According to the gas sensor element having the above structure as the first aspect of the invention, because a plurality of pores in the porous protective layer traps poisoning components, for example, oil containing components such as P, Ca, Zn, and Si, gasoline additive components such as K, Na, Pb, the porous protective layer serves as a poison trapping layer. The presence of the porous protective layer can suppress error working of the gas sensor element.

In addition, even if adhered onto the surface of the gas sensor element, the drop of water diffuses into or permeates pores (as fine holes) formed between the hydrophilic heat resisting particles having a small contact angle without entering pores (as fine holes) formed in the hydrophobic heat resisting particles.

It is thereby possible to promote the moving of the drop of water toward the lateral direction of the porous protective layer, and to prevent a water of drop from moving to the depth direction from the outside into the inside of the porous protective layer. This makes it possible for the drop of water adhered on the surface of the gas sensor element to diffuse into the inside of the porous protective layer without for the drop of water to reach the heater section of a weak thermal shock resistance in the gas sensor element. Accordingly, the present invention can provides the gas sensor element with high durability and suppress the gas sensor element to break by a drop of water.

In accordance with the gas sensor element as a second aspect of the present invention, the hydrophobic heat resisting particles are heat resisting particles having a BET specific area of not more than 10 $m^2/g$, and the hydrophilic heat resisting particles are heat resisting particles having a BET specific area of not less than 10 $m^2/g$.

According to the gas sensor element as the second aspect of the invention, using the hydrophobic heat resisting particles having a decreased specific area can increase an apparent contact angle of the hydrophobic heat resisting particles in the porous protective layer. This makes it possible to further increase a water repellency of the porous protective layer. Furthermore, using the hydrophilic heat resisting particles having an increased specific area can increase an apparent contact angle of the hydrophilic heat resisting particles in the porous protective layer. This makes it possible to further increase absorbency of the hydrophilic heat resisting particles in the porous protective layer.

Therefore a drop of water adhered to the surface of the gas sensor element is absorbed and then diffuses into pores (or fine holes) formed between the hydrophilic heat resisting particles, but does not enter the pores (or fine holes) formed between the hydrophobic heat resisting particles in the porous protective layer. This makes it possible to avoid breaking of the gas sensor element, and increase its durability.

In accordance with the gas sensor element as a third aspect of the present invention, the mixing ratio between the hydrophobic heat resisting particles and the hydrophilic heat resisting particles in the porous protective layer is changed from the outside toward the inside of the porous protective layer.

According to the gas sensor element as the third aspect of the invention, changing the mixing ratio between the hydrophobic heat resisting particles and the hydrophilic heat resisting particles can control the direction of water repellency to a desired direction. This makes it possible to suppress a drop of water adhered on the surface of the gas sensor element from entering into the inside of the gas sensor element. This makes it possible to avoid the gas sensor element breaking, and to increase its durability.

In accordance with the gas sensor element as a fourth aspect of the present invention, the mixing ratio between the hydrophobic heat resisting particles and the hydrophilic heat resisting particles is changed in the porous protective layer so that the mixing ratio of the hydrophobic heat resisting particles is gradually increased toward the inside direction of the porous protective layer, and the ratio of the hydrophilic heat resisting particles is gradually increased toward the outside direction of the porous protective layer.

It is also possible to have a structure in which the mixing ratio of the hydrophobic heat resisting particles is gradually increased toward the outside direction of the porous protective layer, and the ratio of the hydrophilic heat resisting particles is gradually increased toward the inside direction of the porous protective layer.

According to the gas sensor element as the fourth aspect of the present invention, a drop of water adhered onto the surface of the gas sensor element diffuses in an area which is close to the outside surface of the porous protective layer. That is, this structure of the porous protective layer in the gas sensor element makes it possible to prevent the drop of water from entering into deep inside of the porous protective layer. This makes it possible to avoid the gas sensor element breaking, and to extremely increase its durability.

In accordance with the gas sensor element as a fifth aspect of the present invention, the porous protective layer has a multilayered structure in which a plurality of layers is laminated. In particular, the porous protective layer contains layers of a high mixing ratio of the hydrophobic heat resisting particles, and layers of a high mixing ratio of the hydrophilic heat resisting particles. The mixing ratio of the hydrophobic heat resisting particles and the hydrophilic heat resisting particles is gradually changed in the plurality of layers forming the porous protective layer.

According to the gas sensor element as the fifth aspect of the invention, the multilayered structure of the porous protective layer containing the layers of a rich hydrophilic heat resisting particle and the layers of a rich hydrophobic heat resisting particles can certainly suppress a drop of water from entering a deep inside of the porous protective layer and the inside of the gas sensor element. This makes it possible to increase its durability.

In accordance with the gas sensor element as a sixth aspect of the present invention, the gas sensor element has a longitudinal shape, and the porous protective layer has a structure in which the mixing ratio of the hydrophobic heat resisting particles is increased toward a front end part of the gas sensor element along an axial direction of the gas sensor element which is placed in and exposed to the flow of the target detection gas, and the mixing ratio of the hydrophilic heat resisting particles is increased toward the distal end of the gas sensor element.

According to the gas sensor element as the sixth aspect of the invention, this structure of the gas sensor element makes a drop of water rapidly diffusing from the front end part toward the distal end part of the gas sensor element. In general, the front end part of the gas sensor element as a gas sensor works under a high temperature condition, and there is a possibility for the front end part of the gas sensor element to break because of being placed and exposed into the flow of a target detection gas such as an exhaust gas emitted from an internal combustion engine. The distal end part of the gas sensor element has also a possibility of breaking by diffusing of the drop of water even if it has a low temperature when compared with the front end part thereof. Therefore this structure of the sixth aspect of the present invention makes it possible to further avoid the gas sensor element breaking, and to increase its durability.

In accordance with the gas sensor element as a seventh aspect of the present invention, the hydrophilic heat resisting particles are made of a metal oxide selected from alumina $Al_2O_3$, spinel $MgO.Al_2O_3$, silica $SiO_2$, or titanium oxide $TiO_2$. In particular, the hydrophobic heat resisting particles are:

(a) made of a metal carbide selected from silicon carbide SiC, tantalum carbide TaC, tungsten carbide WC, and titanium carbide TiC;

(b) made of a metal nitride selected from silicon nitride $Si_3N_4$, and titanium nitride TiN; or (c) made of a metal boride selected from titanium boride TiB and zirconium boride $ZrB_2$.

This structure of the gas sensor element makes it possible for the drop of water adhered on the surface of the gas sensor element to rapidly diffuse into the hydrophilic heat resisting particles in the porous protective layer, and thereby further avoid the gas sensor element breaking, and to increase its durability.

Still further, according to the seventh aspect of the invention, because the hydrophobic heat resisting particles have a high thermal conductivity when compared with that of the hydrophilic heat resisting particles, the hydrophobic heat resisting particles rapidly absorb the thermal shock generated when a drop of water is adhered onto the surface of the gas sensor element. This can suppress propagation of the thermal shock to the heater section and the upper side of the sensor section forming the gas sensor element. This structure of the gas sensor element makes it possible to further avoid the gas sensor element breaking, and to increase its durability.

The present invention provides a gas sensor as an eighth aspect of the present invention. The gas sensor has one of the gas sensor elements previously described. The gas sensor is capable of detecting a concentration of a specific gas component contained in a target detection gas. The gas sensor is placed in a gas flow passage through which the target detection gas flows. The gas sensor has the gas sensor element, a housing, and a cover body. The housing supports a detection part of the gas sensor element with the porous protective layer in the flow of the target detection gas. The cover body has a gas intake hole through which the target detection gas is introduced into the inside of the gas sensor element while protecting the sensor section of the gas sensor element.

According to the gas sensor as the eighth aspect of the invention, even if a drop of water enters the inside of the gas sensor through the gas intake hole while introducing a target detection gas, the drop of water rapidly diffuses in the porous protective layer of the gas sensor element. This can relax a thermal shock and prevent the propagation of the thermal shock into the inside of the gas sensor element. This structure of the gas sensor with the gas sensor element makes it possible to avoid the gas sensor element breaking, and to increase its reliability and durability.

BRIEF DESCRIPTION OF THE DRAWINGS

A preferred, non-limiting embodiment of the present invention will be described by way of example with reference to the accompanying drawings, in which.

DETAILED DESCRIPTION OF THE PREFERRED EMBODIMENTS

Hereinafter, various embodiments of the present invention will be described with reference to the accompanying drawings. In the following description of the various embodiments, like reference characters or numerals designate like or equivalent component parts throughout the several diagrams.

First Embodiment

A description will be given of a gas sensor element and a gas sensor equipped with the gas sensor element according to a first embodiment of the present invention with reference to drawings.

The gas sensor equipped with the gas sensor element according to the invention can be applied to an exhaust gas purifying system for internal combustion engines such as vehicle engines. The gas sensor of the invention is placed in an exhaust gas passage through which an exhaust gas emitted from an internal combustion engine is passed. The gas sensor element detects a concentration of a specific gas component, such as nitrogen oxide ($NO_x$), ammonia ($NH_3$), hydro carbon (HC), contained in an exhaust gas in order to control the combustion control of the internal combustion engine and the exhaust gas purifying system.

A description will now be given of the gas sensor element 10 according to the first embodiment of the invention with reference to FIG. 1A and FIG. 1B. The gas sensor element 10 is an oxygen sensor as a typical gas sensor.

Figure 1A:
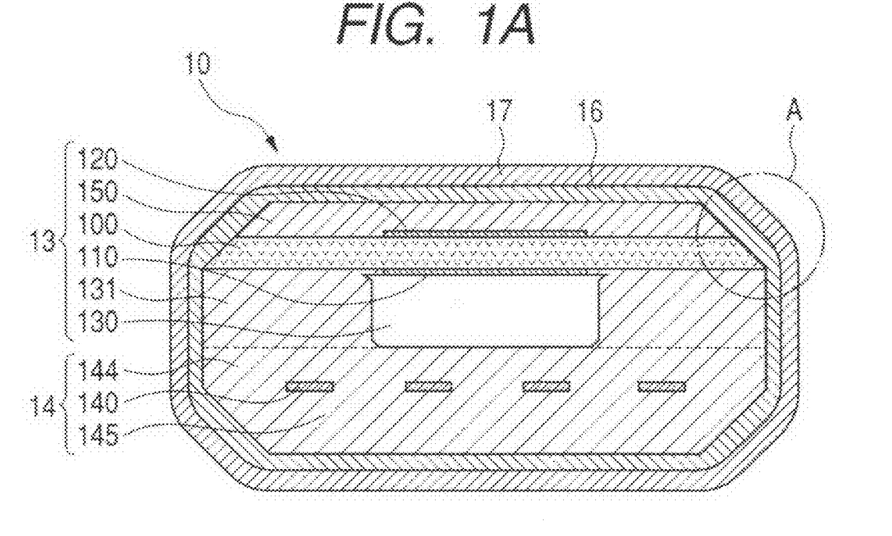
FIG. 1A is a cross section showing a gas sensor element according to the first embodiment of the present invention.

FIG. 1A is a cross section showing the gas sensor element 10 according to the first embodiment of the present invention. FIG. 1B is a cross section showing an enlarged part, which is designated by the reference character "A", in the gas sensor element 10 shown in FIG. 1A.

As shown in FIG. 1A, the gas sensor element 10 is composed of a plate-like sensor section 13 and a heater section 14 which are laminated. The gas sensor element 10 has a longitudinal shape. The outer peripheral surface of the gas sensor element 10 is covered with a porous protective layer. This porous protective layer is made of a mixture composed of at least two kinds of heat resisting particles which have a different contact angle. For example, the porous protective layer is made of a mixture composed of at least one kind of hydrophobic heat resisting particles and at least one kind of hydrophilic heat resisting particles.

The porous protective layer is a main part of the gas sensor element 10 according to the present invention. The porous protective layer is composed of a hydrophobic porous protective layer 16 and a hydrophilic porous protective layer 17. The hydrophobic porous protective layer 16 is made of hydrophobic heat resisting particles 160. The hydrophilic porous protective layer 17 is made of hydrophilic heat resisting particles 170.

The sensor section 13 is comprised of a solid electrolyte layer 100, a detection electrode layer 120, a porous diffusion resistance layer 150, a reference electrode layer 110, and a reference electrode chamber formation layer 131.

The solid electrolyte layer 100 has a plate-like shape, and is made of oxygen ion conductive solid electrolyte material such as yttria-stabilized zirconia (YSZ). The detection electrode layer 120 is formed on the surface of the solid electrolyte layer 100, which is contacted with a target detection gas. The porous diffusion resistance layer 150 is laminated at the detection electrode layer 120 side on the surface of the solid electrolyte layer 100. The target gas is passed under a predetermined diffusion resistance through the porous diffusion resistance layer 150. The reference electrode layer 110 is formed on the other surface of the solid electrolyte layer 100, and contacted with an atmosphere which is introduced in the gas sensor element 10 as a reference gas. The reference electrode chamber formation layer 131 is formed at the reference electrode layer 110 side in order to form a reference gas chamber 130.

The sensor section 13 serves as a detection section, and is composed of the solid electrolyte layer 100 and a pair of electrodes composed of the detection electrode layer 120 and the reference electrode layer 110.

On the other hand, a heater section 14, which heats and activates the sensor section 13, is comprised of a heating body 140. This heating body 140 is laminated in the inside of a plate-like insulation base body 144 and a plate-like insulation base body 145.

Corners of the sensor section 13 and the heater section 14 are chamfered along a longitudinal direction of the gas sensor element 10 in order to avoid a thermal stress concentration and relax strain.

As shown in FIG. 1E, the hydrophobic porous protective layer 16 is a porous body made of the hydrophobic heat resisting particles 160. The surface of the sensor section 13 and the surface of the heater section 14 are covered with the hydrophobic porous protective layer 16.

For example, the hydrophilic heat resisting particles 170 are made of a metal oxide which is selected from alumina $Al_2O_3$, spinel $MgO.Al_2O_3$, silica $SiO_2$, or titanium oxide $TiO_2$.

It is possible to use the hydrophilic heat resisting particles 170 having a particle size within a range of 10 nm to 0.2 μm in average particle diameter. A "BET" (Brunauer, Emmet and Teller) specific area of the hydrophilic heat resisting particle 170 is not less than 10 $m^2$/g and not more than 100 $m^2$/g. A true contact angle of the hydrophilic heat resisting particle 170 to a water droplet (or a drop of water) is not more than 30°

Figure 2A:
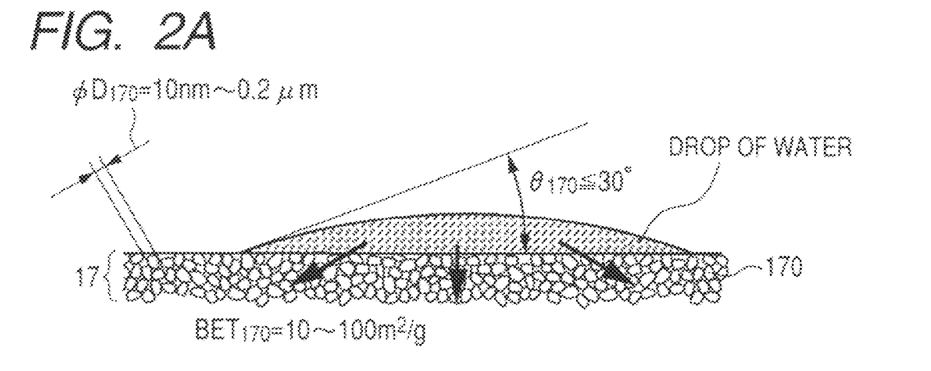
FIG. 2A is a schematic view showing a state in which hydrophilic heat resisting particles are contacted to drops of water in order to show an effect of the gas sensor element according to the first embodiment of the present invention.
Figure 2B:
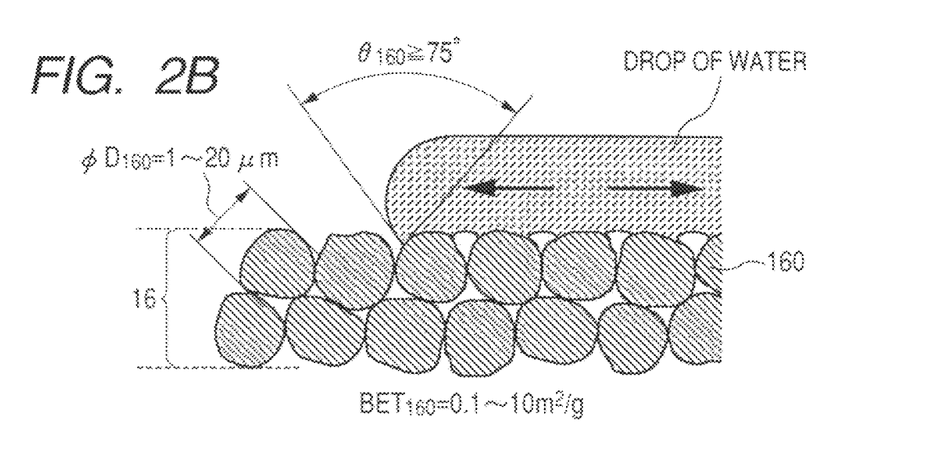
FIG. 2B is a schematic view showing a state in which hydrophobic heat resisting particles are contacted to a drop of water.
Figure 2C:
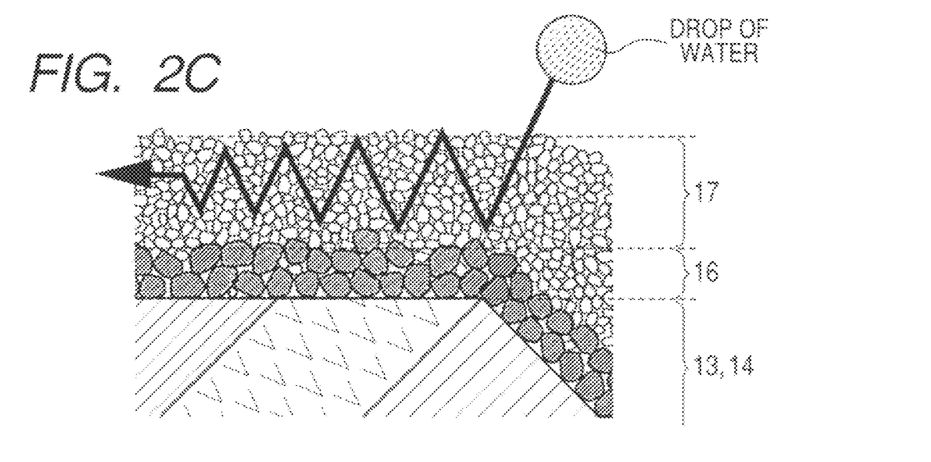
FIG. 2C is a schematic view showing a state in which a drop of water diffuses through a hydrophilic porous protective layer in the gas sensor element according to the first embodiment of the invention.

FIG. 2A is a schematic view showing a state in which the hydrophilic heat resisting particles 170 contact to a drop of water in order to show an effect of the gas sensor element 10 according to the first embodiment. FIG. 2B is a schematic view showing a state in which the hydrophobic heat resisting particles 160 contact to a drop of water, FIG. 2C is a schematic view showing a state in which a drop of water diffuses through the hydrophilic porous protective layer 17 in the gas sensor element 10 according to the first embodiment of the invention.

As shown in FIG. 2A, an apparent contact angle of the hydrophilic porous protective layer 17 to a drop of water is not more than 20°. This size of the apparent contact angle of the hydrophilic heat resisting particle 170 to a drop of water becomes extremely small in detection because the drop of water rapidly diffuses by a capillary phenomenon by pores or fine holes formed between the hydrophilic heat resisting particles 170.

For example, the hydrophobic heat resisting particles 160 are made of metal carbide which is selected from silicon carbide SiC, tantalum carbide TaC, tungsten carbide WC, and titanium carbide TiC, or made of a metal nitride which is selected from silicon nitride $Si_3N_4$, and titanium nitride TiN, or made of a metal boride which is selected from titanium boride TiB, and zirconium boride $ZrB_2$.

It is possible to use the hydrophobic heat resisting particles 160 having a particle size within a range in average particle diameter of 1 μm to 20 μm. A "BET" specific area of the hydrophobic heat resisting particle 160 is not less than 0.1 $m^2$/g and not more than 10 $m^2$/g. A true contact angle of the hydrophobic heat resisting particles 160 to a drop of water is not less than 75°. As shown in FIG. 2B, because the hydrophobic heat resisting particle 160 has a large contact angle to a drop of water, the drop of water remains on the surface of the hydrophobic porous protective layer 16 without entering between the pores (or fine holes) formed between the hydrophobic heat resisting particles 160.

As shown in FIG. 2C, when a drop of water is attached onto the surface of the gas sensor element 10, the drop of water diffuses into the inside of the hydrophilic porous protective layer 17 without entering the inside of the hydrophobic porous protective layer 16. Accordingly, even if the heater section 14 heats the inside of the gas sensor element 10 by supplying an electric power, any drop of water does not directly contact to both the sensor section 13 and the heater section 14. That is, because the drop of water is evaporated in the inside of the hydrophilic porous protective layer 17, it is possible to avoid the sensor section 13 and/or the heater section 14 breaking.

A description will now be given of experimental results regarding the conditions of breaking the gas sensor element by a drop of water. The experiment was performed under different conditions in heating energy to heat the gas sensor element and an amount of water droplets.

The experiment prepared three samples E1, E2, and E3 and four comparison samples C1, C2, C3, and C4. The three samples E1, E2, and E3 have the structure of the gas sensor element 10 according to the present invention. Those four comparison samples C1, C2, C3, and C4 had a structure without forming any hydrophobic porous protective layer. That is, each of the four comparison samples C1, C2, C3, and C4 had a hydrophilic porous protective layer, and did not have any hydrophobic porous protective layer.

Table 1 shows the experimental results. As clearly understood from Table 1, breaking caused by the presence of a drop of water did not occur in the samples E1, E2, and E3 under a condition to cause the four comparison is samples C1, C2, C3, and C4 breaking.

TABLE 1

| Samples | Presence of hydrophilic porous protective layer | Temperature (° C.) of gas sensor element (sample) | Amount (μL) of water droplets | Occurring of breaking |
|---|---|---|---|---|
| E1 | present | 700 | 0.02 | none |
| E2 | present | 700 | 0.2 | none |
| E3 | present | 600 | 1. | none |
| C1 | none | 700 | 0.02 | none |
| C2 | none | 700 | 0.2 | 1/2 |
| C3 | none | 600 | 1 | 1/2 |
| C4 | none | 700 | 1 | 1 |

A description will now be given of a method of producing the gas sensor element 10 according to the first embodiment of the invention with reference to FIG. 3 and FIGS. 4A, 4B, 4C, and 4D.

Figure 3:
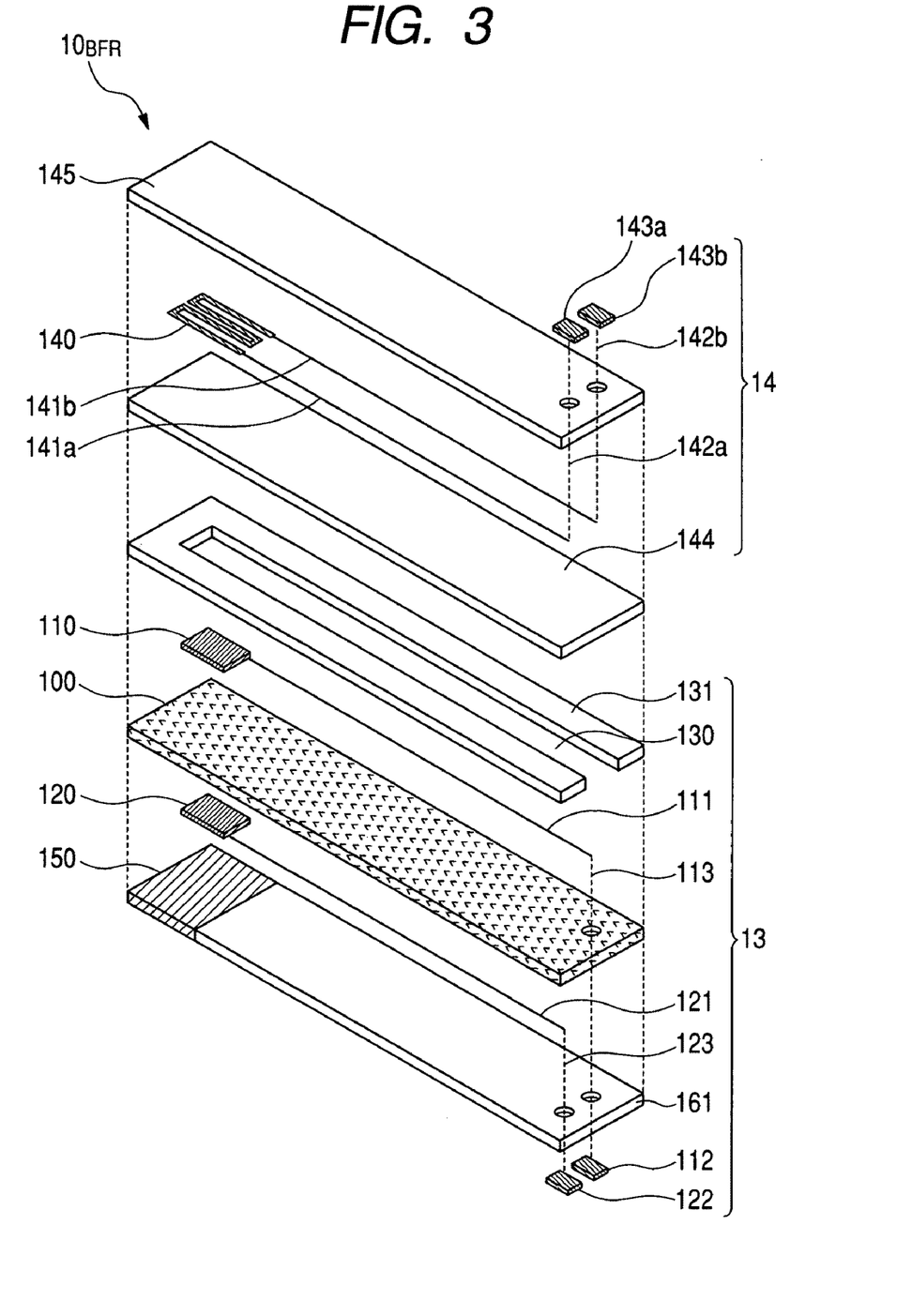
FIG. 3 is a perspective elevation view showing a structure of the gas sensor element before forming a hydrophobic porous protective layer and the hydrophilic porous protective layer according to the first embodiment of the present invention.
Figures 4A, 4B, 4C, 4D:
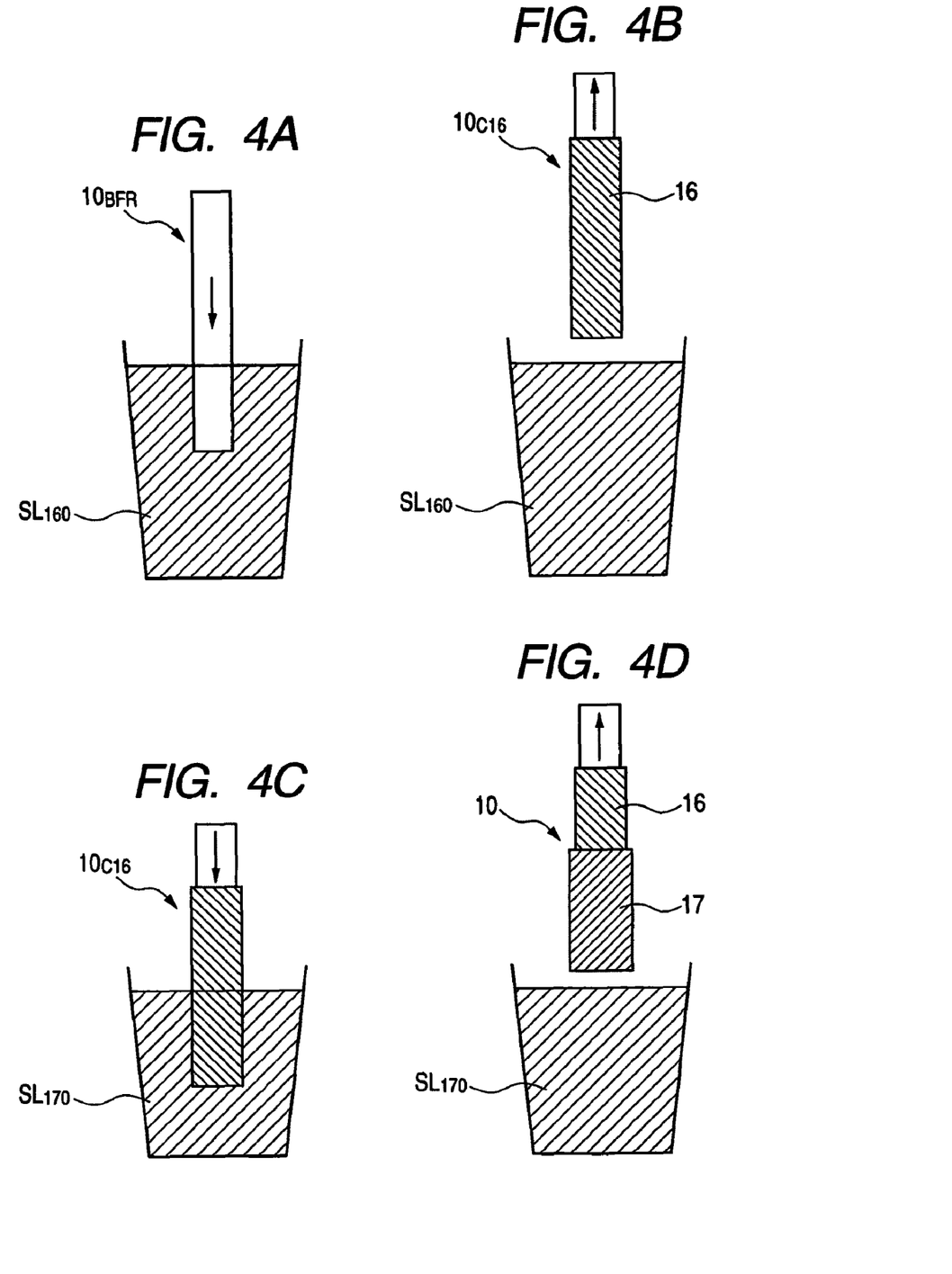
FIG. 4A, FIG. 4B, FIG. 4C, and FIG. 4D show a method of forming the hydrophobic porous protective layer and the hydrophilic porous protective layer in the gas sensor element according to the first embodiment of the present invention.

FIG. 3 is a perspective elevation view showing a structure of the gas sensor element $10_{BFR}$ before forming the hydrophobic porous protective layer 16 and the hydrophilic porous protective layer 17 according to the first embodiment of the invention. That is, FIG. 3 shows a structure of the gas sensor element $10_{BFR}$ before forming the hydrophobic porous protective layer 16 and the hydrophilic porous protective layer 17.

FIGS. 4A, 4B, 4C, and 4D show a method of forming the hydrophobic porous protective layer 16 and the hydrophilic porous protective layer 17 in the gas sensor element 10 according to the first embodiment of the invention.

As shown in FIG. 3, the solid electrolyte layer 100 is produced by making slurry and then shaping the slurry into a sheet-like body by doctor blade method. The slurry is made by dipersing oxygen ion conductive solid electrolyte material such as yttria stabilized zirconia (YSZ), plasticizer such as di-butyl phthalate (DBP), and dispersant into a dispersing medium such as toluene and ethanol.

The detection electrode layer 120 and a detection electrode lead section 121 are formed on the surface of the solid electrolyte layer 100 at the target gas side to be detected. The reference electrode layer 110 and a reference electrode lead section 111 are printed on the other surface of the solid electrolyte layer 100. The printing step uses a paste made of a mixture of platinum (Pt) paste and the slurry. This slurry is used to form the solid electrolyte layer 100.

The reference gas chamber 130 is formed by shaping slurry into a sheet-like layer by the doctor blade method, where the slurry is obtained by dispersing insulation ceramic material such as alumina, PBV, DBP, and dispersing agent into a dispersing medium. A plurality of the sheet-like layers is punched by using a metal die. A plurality of the character "U"-like sheets after the punching step are laminated to each other in order to produce the reference-gas chamber formation layers 131.

The insulation ceramics sheet is used as the plate-Like insulation base body 145. A paste made of a mixture of Pt paste and alumina slurry is printed on one surface of the plate-like insulation body 145 in order to form the heating body 140 and heating-body lead sections 141a and 141b. The paste is also printed on the other surface of the plate-like insulation base body 145 in order to form a pair of heating-body terminals 143a and 143b.

A pair of through-hole electrodes 142a and 142b is formed in a pair of through-holes formed in the plate-like insulation base body 145 by a suction printing method. The through-hole electrodes 142a and 142b electrically contact the heating-body lead sections 141a and 141b with the heating-body terminals 143a and 143b, respectively. An insulation base body 144 is laminated on the plate-like insulation base body 145 at the heating body formation side at which the heating body 140 is formed. This makes the heater section 14 which embeds the heating body 140 therein.

The porous diffusion resistance layer 150 is formed at the detection electrode layer 120 side of the solid electrolyte layer 100 by using a slurry, where the slurry is made by dispersing heat resisting ceramics material and a binder into a dispersing medium, and this heat resisting ceramics material is alumina having a large diameter or size rather than that of the alumina sheet previously described.

Figure 5:
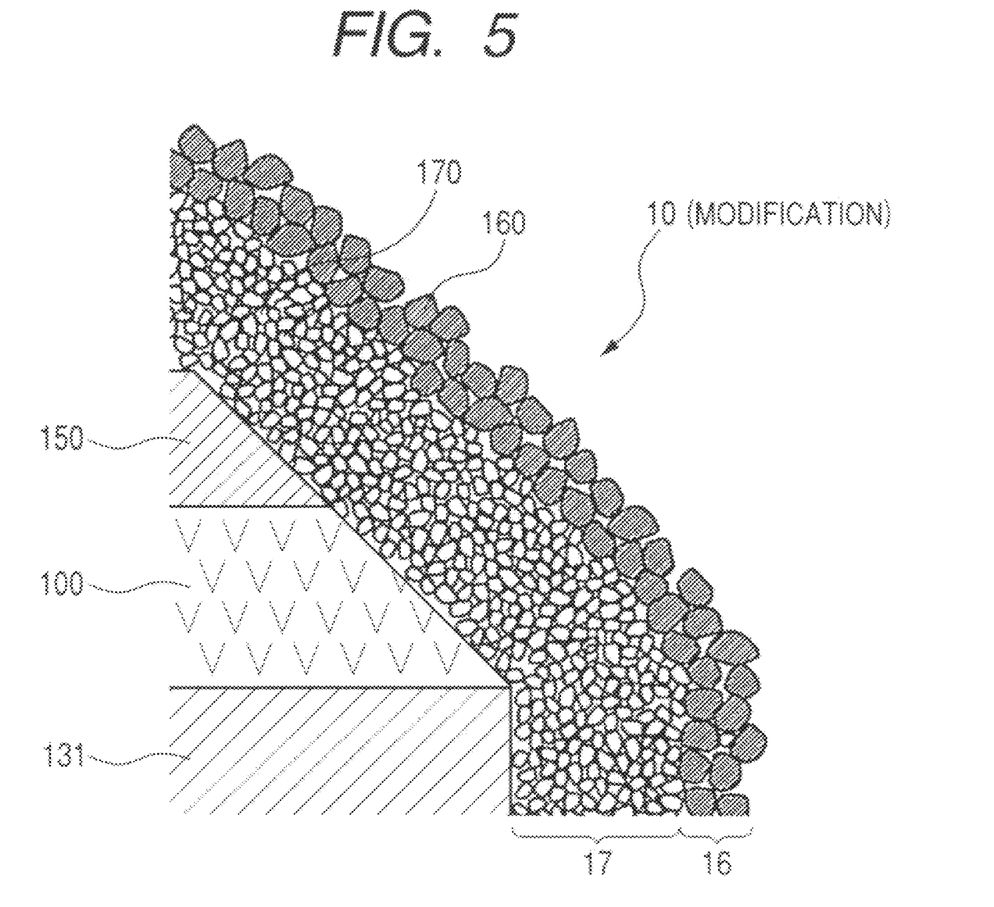
FIG. 5 is a cross section showing an enlarged part in a modification of the gas sensor element shown in FIG. 1A.

As shown in FIG. 5, it is possible to use the plate-like porous diffusion resistance layer 150 or print the porous diffusion resistance layer 150 so that the detection electrode layer 120 is covered with the porous diffusion resistance layer 150.

A diffusion preventing layer 161 is formed at the distal end part of the porous diffusion resistance layer 150 so that the detection electrode lead section 121 is covered with the diffusion preventing layer 161 by using the insulation ceramics sheet previously described.

A detection electrode terminal section 122 and a reference electrode terminal section 112 are printed to form them on the surface of the diffusion preventing layer 161.

A through-hole electrode 123 and a through-hole electrode 113 are formed in the porous diffusion resistance layer 150 by a suction printing method, where the through-hole electrode 123 electrically contacts the detection electrode lead section 121 with the detection electrode terminal section 122, and the through-hole electrode 113 electrically contacts the reference electrode lead section 111 with the reference electrode terminal section 112.

The sensor section 13 and the heater section 14 are laminated by the above method, and the lamination body is then dried and fired to produce the gas sensor element $10_{BFR}$ before forming the hydrophobic porous protective layer 16. It is also possible to use an adhesion paste made by optionally mixing materials forming each layer in order to make the lamination body. It is also possible to produce the lamination body by a thermal pressing method.

As shown in FIGS. 4A, 4B, 4C, and 4D in order, hydrophobic slurry $SL_{160}$ is prepared by dispersing the hydrophobic heat resisting particles 160, a dispersing agent, and inorganic binder into dispersing medium such as water or organic solvent. The gas sensor element $10_{BFR}$ is then immersed into the hydrophobic slurry $SL_{160}$ in order to cover a predetermined part of the gas sensor element $10_{BFR}$ with the hydrophobic heat resisting particles 160. This makes the gas sensor element $10_{C16}$ with the hydrophobic porous protective layer 16. The gas sensor element $10_{C16}$ is then dried.

Further, a hydrophilic slurry $SL_{170}$ is prepared by dispersing the hydrophilic heat resisting particles 170, a dispersing agent, and inorganic binder into dispersing medium such as water or organic solvent. The gas sensor element $10_{C16}$ is then immersed into the hydrophilic slurry $SL_{170}$ in order to cover a predetermined part of the gas sensor element $10_{C16}$ with the hydrophilic heat resisting particles 170 to form the hydrophilic porous protective layer 17. This makes the gas sensor element $10_{C16}$ with the hydrophilic porous protective layer 17. The gas sensor element $10_{C16}$ is then dried to form the gas sensor element 10. It is also possible to fire the hydrophobic porous protective layer 16 and the hydrophilic porous protective layer 17 according to demands.

FIG. 5 is a cross section showing an enlarged part in a modification of the gas sensor element 10 shown in FIG. 1A.

In the first embodiment, the hydrophilic porous protective layer 17 is formed on the surface of the hydrophobic porous protective layer 16 in the gas sensor element 10 of the first embodiment.

Figure 1B:
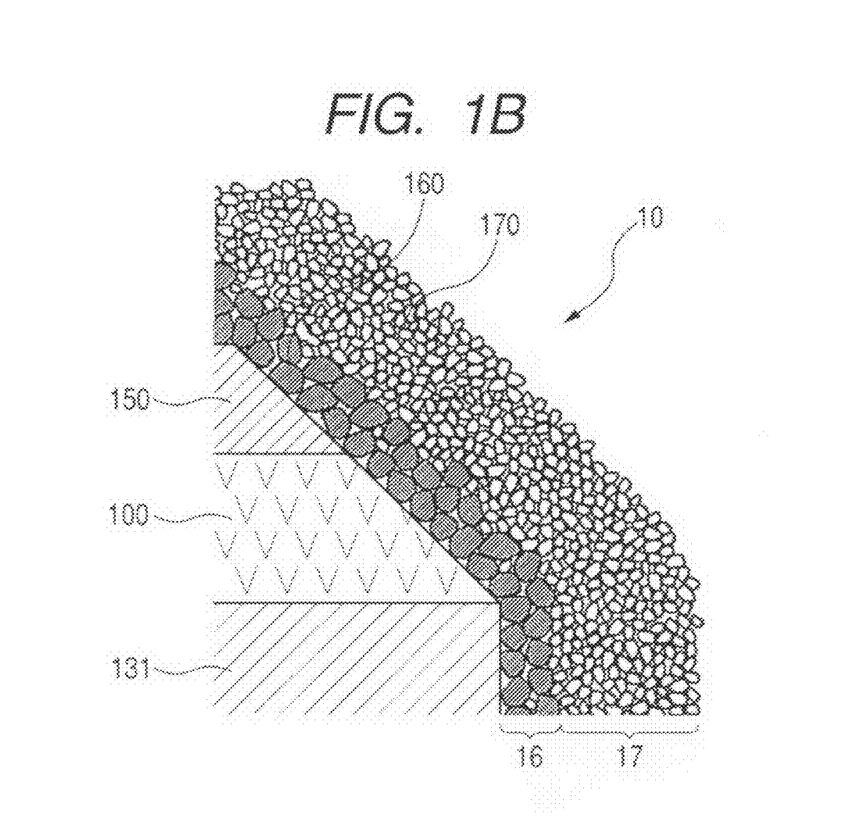
FIG. 1B is a cross section showing an enlarged part, which is designated by the reference character "A", in the gas sensor element shown in FIG. 1A.

However, the present invention is not limited by the structure of the gas sensor element 10 of the first embodiment shown in FIG. 1B. It is possible to form the hydrophobic porous protective layer 16 on the surface of the hydrophilic porous protective layer 17. This structure of the modification of the gas sensor element 10 can prevent a drop of water from entering and diffusing the inside of the gas sensor element 10 by the presence of the hydrophobic porous protective layer 16. Other components of the modification shown in FIG. 5 are the same in structure of those shown in FIG. 1B, the explanation of the same components of the gas sensor element 10 is omitted here.

Second Embodiment

A description will now be given of a gas sensor element 10-1 according to the second embodiment of the present invention with reference to FIG. 6.

Figure 6:
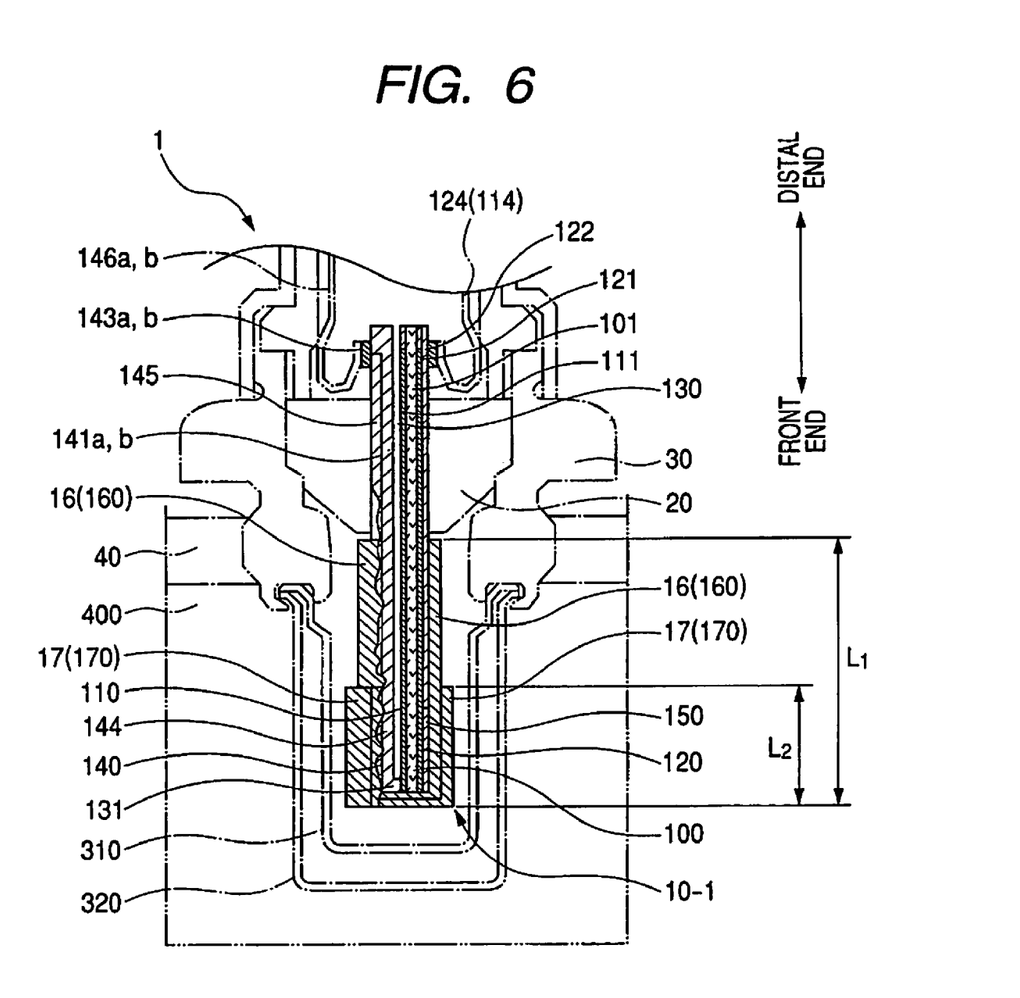
FIG. 6 is a schematic cross section showing a gas sensor element according to a second embodiment of the present invention.

FIG. 6 is a schematic cross section showing the gas sensor element 10-1 according to the second embodiment of the present invention.

As shown in FIG. 6, the gas sensor element 10-1 according to the second embodiment has a structure in which the hydrophobic porous protective layer 16 has a length L2 and the hydrophilic porous protective layer 17 has a length L1 measured in the longitudinal direction of the gas sensor element 10-1.

As shown in FIG. 6, the gas sensor element 10-1 of the second embodiment is placed in a housing 30 through an insulation sealing member 20 and etc. That is, the housing 30 accommodates the gas sensor element 10-1. The housing 30 will be explained later. The gas sensor element 10-1 is supported by and fixed to a wall 40 of the detection target gas passage 400 through the housing 30. A front end part of the gas sensor element 10-1 is placed in the gas passage 400 through which the target detection gas is flowing. Thus, metal covering parts 310 and 320 cover the gas sensor element 10-1 to protect them. Each of the metal covering parts 310 and 320 has one or more introduction holes through which the target detection gas is introduced into the inside of the gas sensor element 10-1, and reaches the detection section of the gas sensor element 10-1.

The heating body 140 is placed at the front end part of the part of the gas sensor element 10-1, which is exposed to the target detection gas. When receiving an electric power, the heating body 40 becomes a high temperature, and both the plate-like sensor section 13 and the heater section 14 are easy to break by a thermal shock. However, both the hydrophobic porous protective layer 16 and the hydrophilic porous protective layer 17 are formed within the range L2 shown in FIG. 6 in the gas sensor element 10-1. This structure of the gas sensor element 10-1 can relax the thermal shock even if a drop of water is adhered onto the part designated by the range L2 because the drop of water is rapidly diffused in the inside of the hydrophilic porous protective layer 17. That is, the structure of the gas sensor element 10-1 makes it difficult to break Still further, the distal end part of the gas sensor element 10-1 has a relatively low temperature, and thereby makes it difficult to break. Because the distal end part side of the gas sensor element 10-1 is covered with the hydrophobic porous protective layer 16, the surface at the distal end part side thereof can escape a drop of water even if the drop of water contacts. Therefore the structure of the gas sensor element 10-1 according to the second embodiment makes it possible to avoid a local temperature change occurring, and the gas sensor element 10-1 does not thereby break even if a drop of water contacts it.

Third Embodiment

A description will now be given of a gas sensor element 10a according to the third embodiment of the present invention with reference to FIG. 7.

Figure 7:
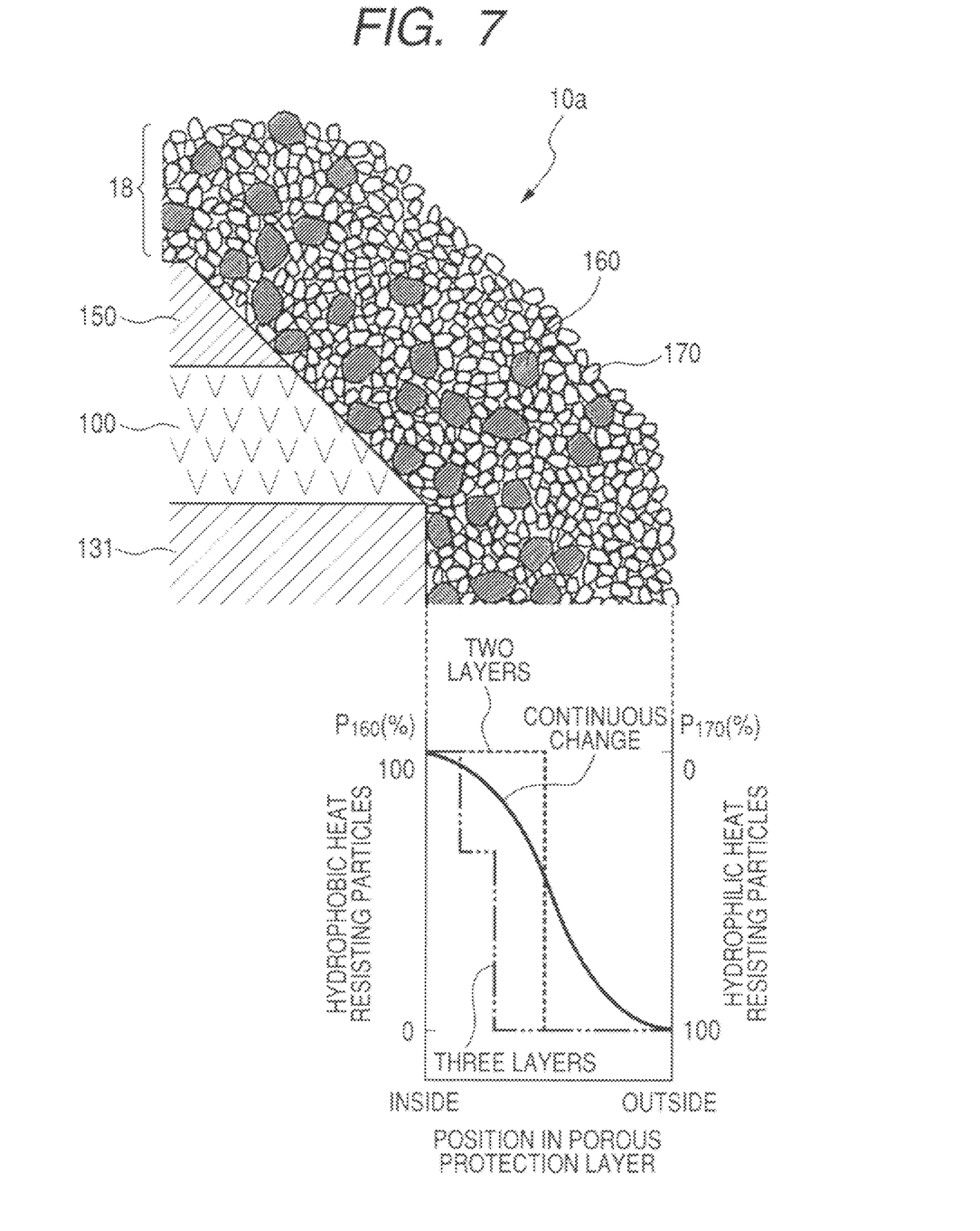
FIG. 7 is a cross section showing an enlarged part in a gas sensor element according to a third embodiment of the present invention.

FIG. 7 is a cross section showing an enlarged part in the gas sensor element 10a according to the third embodiment.

The first and second embodiments show the case of separately forming the hydrophobic porous protective layer 16 and the hydrophilic porous protective layer 17 on the surface of the gas sensor element.

The gas sensor element 10a according to the third embodiment has a porous protective layer 18. That is, the third embodiment makes and uses mixture slurry of the hydrophobic heat resisting particles 160 and the hydrophilic heat resisting particles 170 in order to form the porous protective layer 18.

Like the effect of the gas sensor element according to the first and second embodiments previously described, the structure of the gas sensor element of the third embodiment makes it possible to prevent a drop of water from entering the inside of the gas sensor element 10a. This structure makes it possible to avoid the gas sensor element breaking even if a drop of water is adhered onto the surface of the gas sensor element 10a.

In the structure of the gas sensor element 101, as shown in FIG. 7, a mixing ratio of the hydrophobic heat resisting particles 160 to the hydrophilic heat resisting particles 170 in the porous protective layer 18 is gradually increased from the outside toward the inside of the porous protective layer 18. In other words, the mixing ratio of the hydrophilic heat resisting particles 170 to the mixing ratio of the hydrophobic heat resisting particles 160 is gradually increased from the inside to the outside of the porous protective layer 18.

Figure 11:
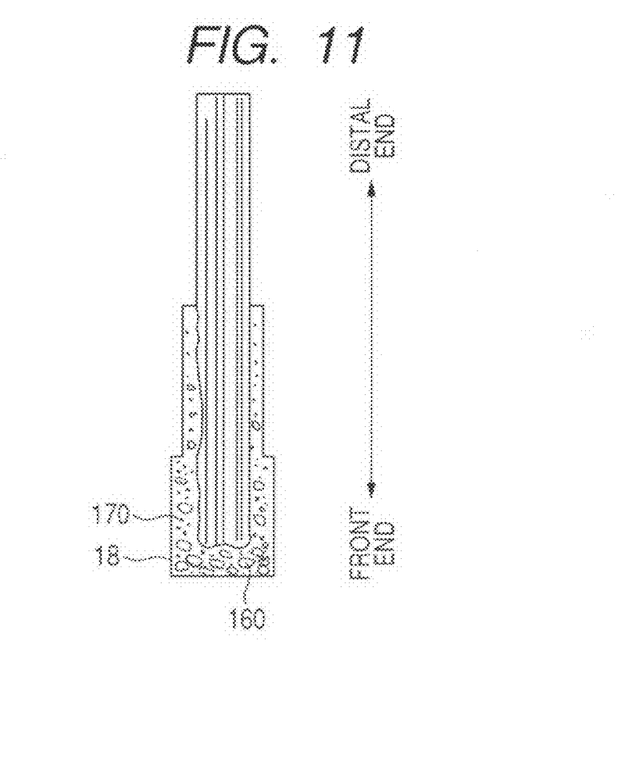
FIG. 11 is a cross section showing another modification of the gas sensor element according to the third embodiment of the present invention.

Still further, the mixing ratio of the hydrophobic heat resisting particles 160 is gradually increased from the bottom side (or the distal end side) toward the front end part in the porous protective layer of the gas sensor element 10a, which is exposed to the target detection gas, along the axial direction of the gas sensor element 10a, as shown in FIG. 11. In other words, the mixing ratio of the hydrophilic heat resisting particles 170 is gradually increased from the front end part toward the distal end part of the gas sensor element 10a along the axial direction of the gas sensor element 10a.

A concrete method of producing the porous protective layer 18 prepares various mixture slurries having a different mixing ratio of the hydrophobic heat resisting particles 160 or the hydrophilic heat resisting particles 170. In the method, the mixture slurries having a different mixing ratio are applied multiple times onto a predetermined part on the surface of the gas sensor element in order to obtain the porous protective layer 18 of a predetermined thickness. This makes it possible to form the porous protective layer 18 in which the mixing ratio of each of the hydrophobic porous protective layer 16 and the hydrophilic porous protective layer 17 is changed.

It is possible for the porous protective layer 18 in the gas sensor element 10a according to the third embodiment to have one of:

(a) a single layer structure in which the mixing ratio between the hydrophobic heat resisting particles 160 and the hydrophilic heat resisting particles 170 is continuously changed in the porous protective layer, as designated by the solid line shown in FIG. 7;

(b) a double-layer structure in which the hydrophobic porous protective layer 16 and the hydrophilic porous protective layer 17 are separately formed, as designated by the dotted line shown, in FIG. 7;

(c) a triple-layer structure in which the innermost layer is made of the hydrophobic porous protective layer 16, the middle layer is made of a mixture of the hydrophobic heat resisting particles 160 and the hydrophilic heat resisting particles 170, and the outermost layer is made of the hydrophilic heat resisting particles 170, as designated by the long dashed and double dotted line; and (d) a structure having not less than three layers in which the mixing ratio between the hydrophobic heat resisting particles 160 and the hydrophilic heat resisting particles 170 is changed.

Figure 8:
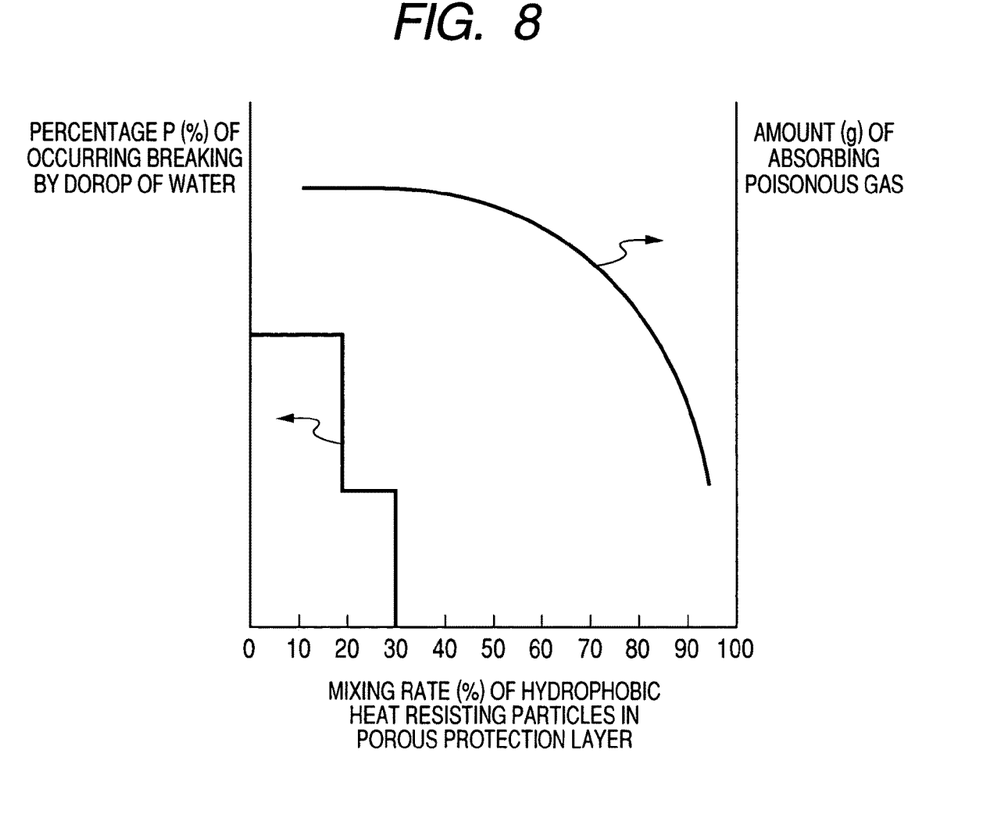
FIG. 8 is a graph showing effects of the gas sensor element according to the third embodiment of the present invention.

FIG. 8 is a graph showing effects of the gas sensor element 10a according to the third embodiment of the present invention.

In the graph shown in FIG. 8, the lateral line indicates the mixing ratio (%) of the hydrophobic heat resisting particles 160 in the porous protective layer 18 along the thickness direction of the gas sensor element. The vertical line at the left side designates a percentage or possibility (%) of breaking by a drop of water, and the vertical line at the right side denotes an amount (g) of absorbed poisoning gas.

As shown in FIG. 8, the more the mixing ratio of the hydrophobic heat resisting particles 160 increases, the more the possibility of breaking of the gas sensor element by contacting to a drop of water decreases. But, the mixing ratio of the hydrophobic heat resisting particles 160 excesses a predetermined range, the ratio of absorbed poisoning gas becomes decreased because an opening diameter of porous formed between the hydrophobic heat resisting particles 160 becomes large.

The experimental results shown in FIG. 8 clearly indicate that a preferred mixing ratio of the hydrophobic heat resisting particles 160 in the porous protective layer 18 is within a range of not less than 20% to not more than 80%, where the hydrophobic heat resisting particles 160 and the hydrophilic heat resisting particles 170 are mixed in the porous protective layer 18.

(Modification)

A description will now be given of a modification of the gas sensor element 10a-1 of the third embodiment with reference to FIG. 9.

Figure 9:
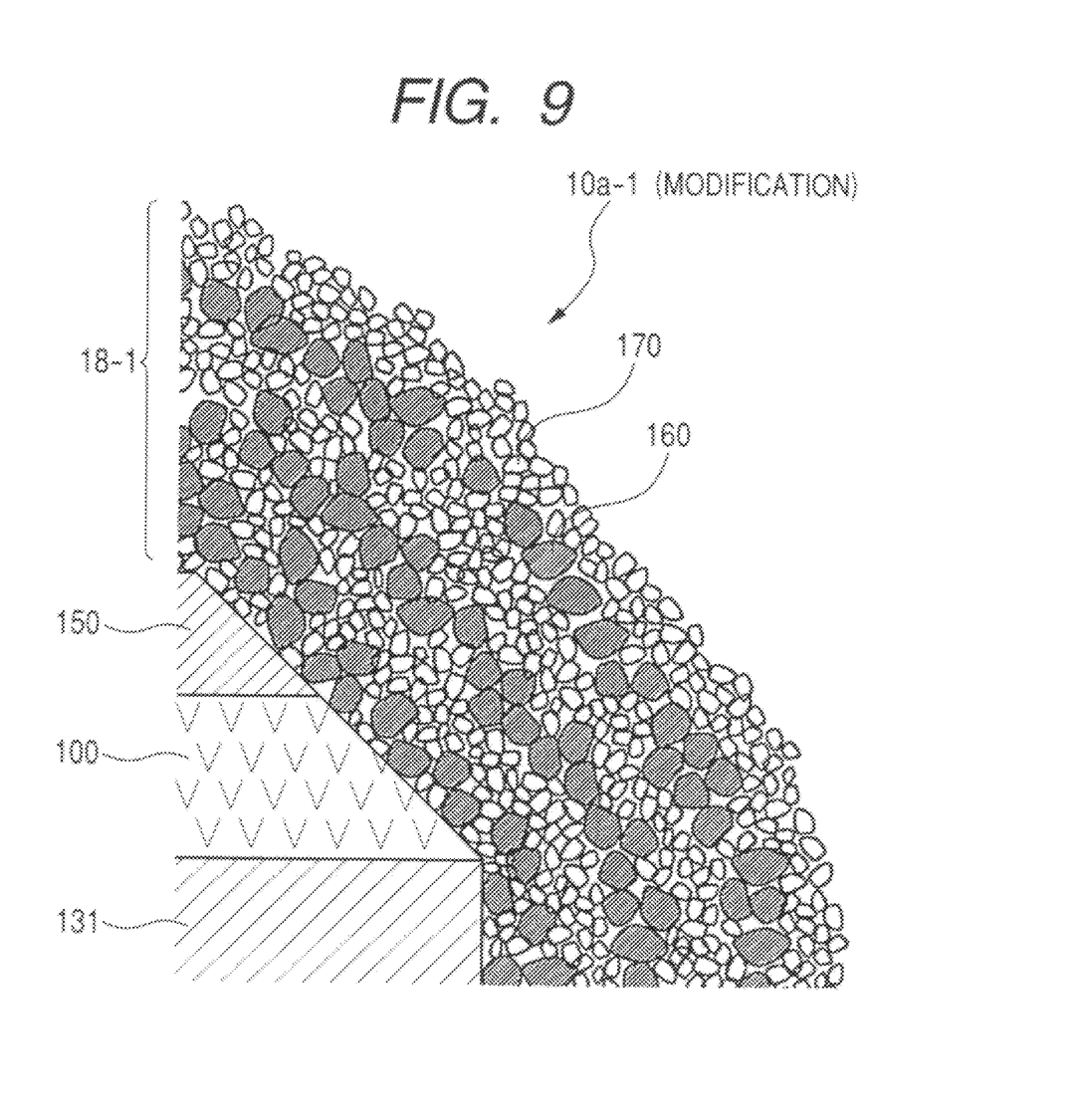
FIG. 9 is a cross section showing an enlarged part in a modification of the gas sensor element according to the third embodiment of the present invention.

FIG. 9 is a cross section showing an enlarged part in the modification of the gas sensor element 10a-1 according to the third embodiment of the present invention.

The porous protective layer 18-1 has a multiple layer structure in which a plurality of the hydrophobic porous protective layer 16 and the hydrophilic porous protective layer 17 are alternately laminated. It is possible to change the mixing ratio of the hydrophobic porous protective layer 16 and the mixing ratio of the hydrophilic porous protective layer 17 in each of the multiple layer structure. In particular, the mixing ratio of the hydrophobic porous protective layer 16 is increased along the direction from the inside layer to the outside layer. It is possible for the outermost layer in the porous protective layer 18-1 to be made of the hydrophobic porous protective layer 16 having the mixing ratio of 100%. In other words, it is possible for the mixing ratio of the hydrophilic heat resisting particles 170 to more increase along the direction to the inside of the porous protective layer 18-1. It is possible for the innermost layer in the porous protective layer 18-1 to be made of the hydrophilic porous protective layer 17 having the mixing ratio of 100%.

This structure makes it possible to completely suppress a drop of water from entering and permeating the inside of the gas sensor element 10a-1 because of having a multilayer structure in which a plurality of the layers of a rich mixing ratio of the hydrophobic heat resisting particles 160 and the layers of a rich mixing ratio of the hydrophilic heat resisting particles 170 is laminated. This structure provides a gas sensor element 10a-1 with high durability and high breaking resistance when a drop of water is adhered onto the surface of the gas sensor element 10a-1.

(Another Modification)

A description will now be given of another modification of the gas sensor element 10a-2 of the third embodiment with reference to FIG. 10.

Figure 10:
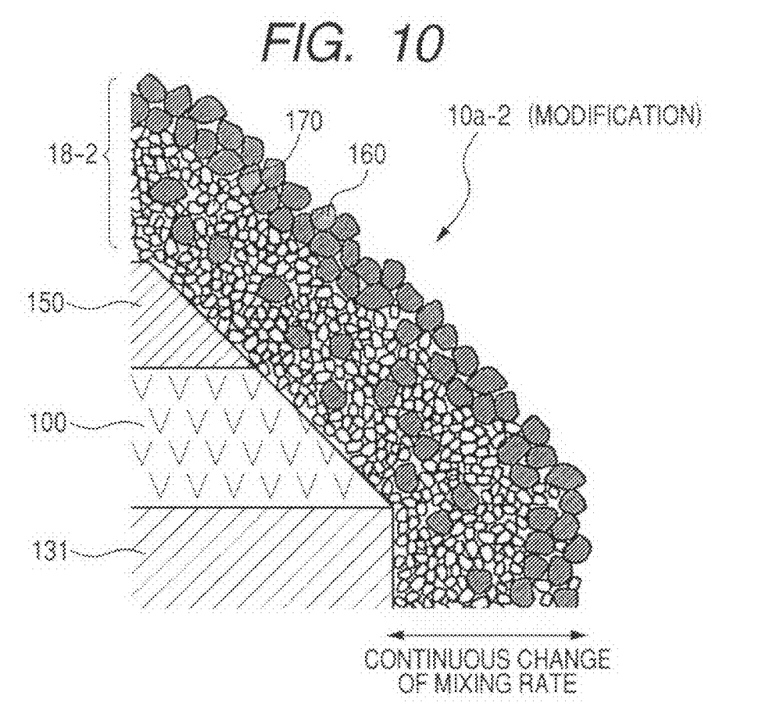
FIG. 10 is a cross section showing an enlarged part in another modification of the gas sensor element according to the third embodiment of the present invention.

FIG. 10 is a cross section showing an enlarged part of another modification of the gas sensor element according to the third embodiment of the present invention.

As shown in FIG. 10, the gas sensor element 10a-2 according to another modification of the third embodiment has a structure in which a mixing ratio of the hydrophobic heat resisting particles 160 and the hydrophilic heat resisting particles 170 is continuously changed from the outside toward the inside of the porous protective layer 18-2. In the structure of the porous protective layer 18-2 shown in FIG. 10, the outermost part has 100% of the hydrophobic heat resisting particles 160, and the innermost part has a 100% of the hydrophilic heat resisting particles 170, and the mixing ratio of both the hydrophobic heat resisting particles 160 and the hydrophilic heat resisting particles 170 is gradually changed along the depth direction of the porous protective layer 18-2.

It is also possible for the gas sensor element 10a-2 to have a structure of the porous protective layer 18-2 in which the outermost part has a 100% of the hydrophilic heat resisting particles 170, and the innermost part has a 100% of the hydrophobic heat resisting particles 160, and the mixing ratio of both the hydrophobic heat resisting particles 160 and the hydrophilic heat resisting particles 170 is gradually changed along the depth direction of the porous protective layer 18-2.

The concept of the present invention is not limited by the embodiments and the modifications previously described. It is possible for the gas sensor element to have another structure of the porous protective layer within the scope of the present invention.

For example, the above embodiments and the modification disclose the gas sensor element which acts as an oxygen sensor having the solid electrolyte layer 100 made of perovskite type transition metal oxide expressed by a general formula $ABO_3$ which is made mainly of $ZrO_2$ or $CeO_2$ and one of CaO, SrO, BaO of a hydrogen ion conductivity. The present invention can be applied to various sensors such as an ammonia sensor, a hydrocarbon sensor, and an oxygen sensor and a NOx sensor composed of a plurality of detection cells in order to increase detection accuracy.

While specific embodiments of the present invention have been described in detail, it will be appreciated by those skilled in the art that various modifications and alternatives to those details could be developed in light of the overall teachings of the disclosure. Accordingly, the particular arrangements disclosed are meant to be illustrative only and not limited to the scope of the present invention which is to be given the full breadth of the following claims and all equivalents thereof.

What is claimed is:

1. A gas sensor element that detects a concentration of a specific gas component contained in a target detection gas, placed in a gas passage through which the target defection gas flows, comprising:
    a sensor section comprising a solid electrolyte layer and a pair of electrodes, where the solid electrolyte layer is made of solid electrolyte material having an electrical conductivity to a specific ion, and the pair of electrodes formed on a surface of the solid electrolyte layer;
    a heater section for heating and activating the sensor section;
    a porous protective layer covering a surface of the sensor section and a surface of the heater section which are exposed to the target detection gas, wherein the porous protective layer is made of a mixture composed of at least one kind of hydrophobic heat resisting particles and at least of one is kind of hydrophilic heat resisting particles which have a different contact angle to a drop of water, and
    wherein the hydrophobic heat resisting particles are heat resisting particles having a BET specific area of not more than 10 $m^2/g$, and the hydrophilic heat resisting particles are heat resisting particles having a BET specific area of not less than 10 $m^2/g$.

2. The gas sensor element according to claim 1, wherein a contact angle of the hydrophobic heat resisting particles is not less than 75°, and a contact angle of the hydrophilic heat resisting particles is not more than 30°.

3. The gas sensor element according to claim 1, wherein the mixing ratio between the hydrophobic heat resisting particles and the hydrophilic heat resisting particles is changed in the porous protective layer so that the mixing ratio is gradually changed from the outside of the porous protective layer to the inside of the porous protective layer.

4. The gas sensor element according to claim 1, wherein the mixing ratio between the hydrophobic heat resisting particles and the hydrophilic heat resisting particles is changed in the porous protective layer so that the mixing ratio of the hydrophobic heat resisting particles is gradually increased toward the inside direction of the porous protective layer, and the ratio of the hydrophilic heat resisting particles is gradually increased toward the outside direction of the porous protective layer.

5. The gas sensor element according to claim 1, wherein the mixing ratio between the hydrophobic heat resisting particles and the hydrophilic heat resisting particles is changed in the porous protective layer so that the mixing ratio of the hydrophobic heat resisting particles is gradually increased toward the outside direction of the porous protective layer, and the ratio of the hydrophilic heat resisting particles is gradually increased toward the inside direction of the porous protective layer.

6. The gas sensor element according to claim 1, wherein the porous protective layer is comprised of a plurality of layers, and the plurality of layers have a different mixing ratio of the hydrophobic heat resisting particles and the hydrophilic heat resisting particles and the different mixing ratio is gradually changed in the plurality of layers.

7. The gas sensor element according to claim 1, wherein the gas sensor element has a longitudinal shape, and the porous protective layer has a structure in which the mixing ratio of the hydrophobic heat resisting particles is increased toward a front end part of the gas sensor element along an axial direction of the gas sensor element which is placed in and exposed to the target detection gas to be detected, and the mixing ratio of the hydrophilic heat resisting particles is increased toward the distal end of the gas sensor element.

8. The gas sensor element according to claim 1, wherein the hydrophilic heat resisting particles are made of a metal oxide selected from alumina $Al_2O_3$, spinel $MgO$—$Al_2O_3$, silica $SiO_2$, or titanium oxide $TiO_2$, and the hydrophobic heat resisting particles are made of one selected from:
    a metal carbide selected from silicon carbide SiC, tantalum carbide TaC, tungsten carbide WC, and titanium carbide TiC;
    a metal nitride selected from silicon nitride $Si_3N_4$, and titanium nitride TiN; and
    a metal boride selected from titanium boride TiB and zirconium boride $ZrB_2$.

9. The gas sensor element according to claim 2, wherein the hydrophilic heat resisting particles are made of a metal oxide selected from alumina $Al_2O_3$, spinel $MgO$—$Al_2O_3$, silica $SiO_2$, or titanium oxide $TiO_2$, and the hydrophobic heat resisting particles are made of one selected from:
    a metal carbide selected from silicon carbide SiC, tantalum carbide TaC, tungsten carbide WC, and titanium carbide TiC;
    a metal nitride selected from silicon nitride $Si_3N_4$, and titanium nitride TiN; and
    a metal boride selected from titanium boride TiB and zirconium boride $ZrB_2$.

10. A gas sensor for detecting a concentration of a specific gas component contained in a target detection gas, which is placed in a gas passage through which the target detection gas flows, comprising:
    the gas sensor element as claimed in claim 1;
    a housing for supporting a detection part of the gas sensor element with the porous protective layer in the flow of the target detection gas; and
    a cover body having a gas intake hole through which the target detection gas is introduced into the inside of the gas sensor element while protecting the sensor section of the gas sensor element.

* * * * *